US009192409B2

(12) United States Patent
Barker

(10) Patent No.: US 9,192,409 B2
(45) Date of Patent: Nov. 24, 2015

(54) STEERABLE STYLET HANDLE ASSEMBLY

(75) Inventor: John Michael Barker, Ventura, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 1436 days.

(21) Appl. No.: 12/356,480

(22) Filed: Jan. 20, 2009

(65) Prior Publication Data

US 2009/0187222 A1 Jul. 23, 2009

Related U.S. Application Data

(60) Provisional application No. 61/022,953, filed on Jan. 23, 2008.

(51) Int. Cl.
| A61B 17/34 | (2006.01) |
| A61B 17/06 | (2006.01) |
| A61N 1/05 | (2006.01) |
| A61B 17/00 | (2006.01) |
| A61N 1/372 | (2006.01) |
| A61N 1/378 | (2006.01) |

(52) U.S. Cl.
CPC ....... *A61B 17/3468* (2013.01); *A61B 17/06109* (2013.01); *A61N 1/0551* (2013.01); *A61B 2017/003* (2013.01); *A61B 2017/00331* (2013.01); *A61N 1/3787* (2013.01); *A61N 1/37264* (2013.01); *Y10T 29/49826* (2013.01)

(58) Field of Classification Search
USPC .......................... 607/2, 128, 46, 48, 116–117
See application file for complete search history.

(56) References Cited

U.S. PATENT DOCUMENTS

| 5,143,540 | A | 9/1992 | Pyzik et al. |
| 5,300,106 | A | 4/1994 | Dahl et al. |
| 5,312,439 | A | 5/1994 | Loeb et al. |
| 5,327,906 | A | 7/1994 | Fideler |
| 5,722,425 | A | 3/1998 | Bostrom et al. |
| 5,741,225 | A | 4/1998 | Lax et al. |
| 5,843,153 | A | 12/1998 | Johnston et al. |
| 6,051,017 | A | 4/2000 | Loeb et al. |
| 6,164,284 | A | 12/2000 | Schulman et al. |
| 6,185,452 | B1 | 2/2001 | Schulman et al. |
| 6,208,894 | B1 | 3/2001 | Schulman et al. |
| 6,249,707 | B1 | 6/2001 | Kohnen et al. |
| 6,356,792 | B1 * | 3/2002 | Errico et al. .................. 607/116 |
| 6,381,496 | B1 | 4/2002 | Meadows et al. |

(Continued)

FOREIGN PATENT DOCUMENTS

| EP | 0715865 A2 | 6/1996 |
| EP | 1048271 A2 | 11/2000 |

(Continued)

*Primary Examiner* — Catherine Voorhees
(74) *Attorney, Agent, or Firm* — Lowe Graham Jones PLLC; Bruce E. Black

(57) ABSTRACT

An exemplary steerable stylet handle assembly includes a housing having first and second side walls defining a channel therebetween, a button in communication with the first and second side walls and configured to move distally and proximally within the channel, and a stylet subassembly having an inner stylet wire located at least partially within an outer tubing. The inner stylet wire has a pre-curved portion and is coupled to a proximal portion of the housing. The outer tubing is coupled to the button. Movement of the button within the channel is configured to selectively expose and cover at least a portion of the pre-curved distal portion of the inner stylet wire with the outer tubing.

20 Claims, 8 Drawing Sheets

(56) References Cited

U.S. PATENT DOCUMENTS

| | | |
|---|---|---|
| 6,425,887 B1 | 7/2002 | McGuckin et al. |
| 6,464,697 B1 * | 10/2002 | Edwards et al. ............... 606/41 |
| 6,553,263 B1 | 4/2003 | Meadows et al. |
| 6,592,559 B1 | 7/2003 | Pakter et al. |
| 6,697,677 B2 | 2/2004 | Dahl et al. |
| 6,760,626 B1 | 7/2004 | Boveja |
| 6,889,833 B2 | 5/2005 | Seiler et al. |
| 6,970,747 B2 | 11/2005 | Kokones et al. |
| 7,063,708 B2 | 6/2006 | Gibson et al. |
| 7,242,977 B2 * | 7/2007 | Partridge et al. ............. 600/374 |
| 7,247,160 B2 | 7/2007 | Seiler et al. |
| 7,328,071 B1 * | 2/2008 | Stehr et al. .................. 607/131 |
| 7,343,206 B2 | 3/2008 | Sage et al. |
| 7,392,095 B2 * | 6/2008 | Flynn et al. .................. 607/127 |
| 7,627,380 B2 * | 12/2009 | Podhajsky et al. ............. 607/99 |
| 7,699,809 B2 * | 4/2010 | Urmey .................... 604/165.02 |
| 7,734,342 B2 * | 6/2010 | Gielen et al. ..................... 607/3 |
| 2002/0147484 A1 | 10/2002 | Dahl et al. |
| 2003/0135253 A1 | 7/2003 | Kokones et al. |
| 2003/0171758 A1 | 9/2003 | Gibson et al. |
| 2004/0124105 A1 | 7/2004 | Seiler et al. |
| 2004/0127765 A1 | 7/2004 | Seiler et al. |
| 2004/0162558 A1 | 8/2004 | Hegde et al. |
| 2004/0215139 A1 | 10/2004 | Cohen |
| 2004/0215305 A1 | 10/2004 | Sage |
| 2005/0021119 A1 | 1/2005 | Sage et al. |
| 2005/0205445 A1 | 9/2005 | Seiler et al. |
| 2006/0058861 A1 | 3/2006 | Gibson et al. |
| 2006/0276680 A1 * | 12/2006 | Seiler et al. ....................... 600/7 |
| 2008/0114433 A1 | 5/2008 | Sage et al. |

FOREIGN PATENT DOCUMENTS

| | | |
|---|---|---|
| WO | WO-99/03722 | 1/1999 |
| WO | WO-02/074211 A1 | 9/2002 |
| WO | WO-03/059440 A2 | 7/2003 |
| WO | WO-2004/058326 A2 | 7/2004 |
| WO | WO-2004/060144 A2 | 7/2004 |
| WO | WO-2004/060205 A2 | 7/2004 |

* cited by examiner

STEERABLE STYLET HANDLE ASSEMBLY

CROSS-REFERENCE TO RELATED APPLICATIONS

The present application claims the benefit of U.S. Provisional Patent Application No. 61/022,953, filed Jan. 23, 2008, which is incorporated herein by reference in its entirety.

BACKGROUND

Spinal cord stimulation (SCS) is a well-accepted clinical method for treating a variety of medical conditions in certain populations of patients. SCS systems typically include an implantable pulse generator (IPG) and at least one stimulating lead with one or more electrodes disposed thereon. The lead may be implanted epidurally near the patient's spine and the IPG may be implanted in a surgically convenient location (e.g., within a subcutaneous pocket created within the torso of the patient). The IPG may then generate and deliver electrical stimulation pulses via the one or more electrodes to the spine in accordance with stimulation parameters configured to treat a particular medical disorder.

It is often difficult for a physician to properly position an electrode lead within the epidural space of the spine. To this end, a number of different insertion tools have been developed to assist physicians in positioning electrode leads and other stimulating members (e.g., catheters) within a patient. For example, a typical insertion tool that has been used is known as a stylet and consists of a flexible tube in which a wire with a pre-curved distal portion. When the pre-curved distal portion of the wire is inside the tube, it is restrained from assuming its pre-curved shape, and when it is positioned outside the tube, it assumes its preset shape. The tube is fastened to a handle through which the wire runs to be accessible for adjustment of its position in the tube. When the stylet wire together with the lead is moved towards a desired implant location within the patient, the physician can, by extending a larger or smaller part of the preshaped end of the wire, position the lead at the desired location.

The handling of this stylet is often difficult and cumbersome. Both hands of the physician are often required to adjust the position of the stylet in relation to the tube. In addition, handling of the stylet is complicated by the fact that the physician wears gloves which easily get wet and slippery during an operation.

SUMMARY

An exemplary steerable stylet handle assembly includes a housing having first and second side walls defining a channel therebetween, a button in communication with the first and second side walls and configured to move distally and proximally within the channel, and a stylet subassembly having an inner stylet wire located at least partially within an outer tubing. The inner stylet wire has a pre-curved portion and is coupled to a proximal portion of the housing. The outer tubing is coupled to the button. Movement of the button within the channel is configured to selectively expose and cover at least a portion of the pre-curved distal portion of the inner stylet wire with the outer tubing.

Methods for facilitating stimulation of a stimulation site within a patient include providing a housing having first and second side walls defining a channel therebetween, providing a button in communication with the first and second side walls and configured to move distally and proximally within the channel, providing a stylet subassembly having an inner stylet wire located at least partially within an outer tubing, coupling a proximal portion of the inner stylet wire to a proximal portion of the housing, coupling a proximal portion of the outer tubing to the button, and moving the button within the channel to selectively expose and cover at least a portion of a pre-curved distal portion of the inner stylet wire with the outer tubing.

BRIEF DESCRIPTION OF THE DRAWINGS

The accompanying drawings illustrate various embodiments of the principles described herein and are a part of the specification. The illustrated embodiments are merely examples and do not limit the scope of the disclosure.

Throughout the drawings, identical reference numbers designate similar, but not necessarily identical, elements.

DETAILED DESCRIPTION

Exemplary steerable stylet handle assemblies are described herein. In some examples, a steerable stylet handle assembly includes a housing having first and second side walls defining a channel therebetween, a button in communication with the first and second side walls and configured to move distally and proximally within the channel, and a stylet subassembly having an inner stylet wire located at least partially within an outer tubing. The inner stylet wire has a pre-curved portion and is coupled to a proximal portion of the housing. The outer tubing is coupled to the button. Movement of the button within the channel is configured to selectively expose and cover at least a portion of the pre-curved distal portion of the inner stylet wire with the outer tubing. In this manner, a physician or other handler may more easily and precisely position a stimulating member (e.g., a lead or a catheter) at a stimulation site within a patient.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

Figure 1:
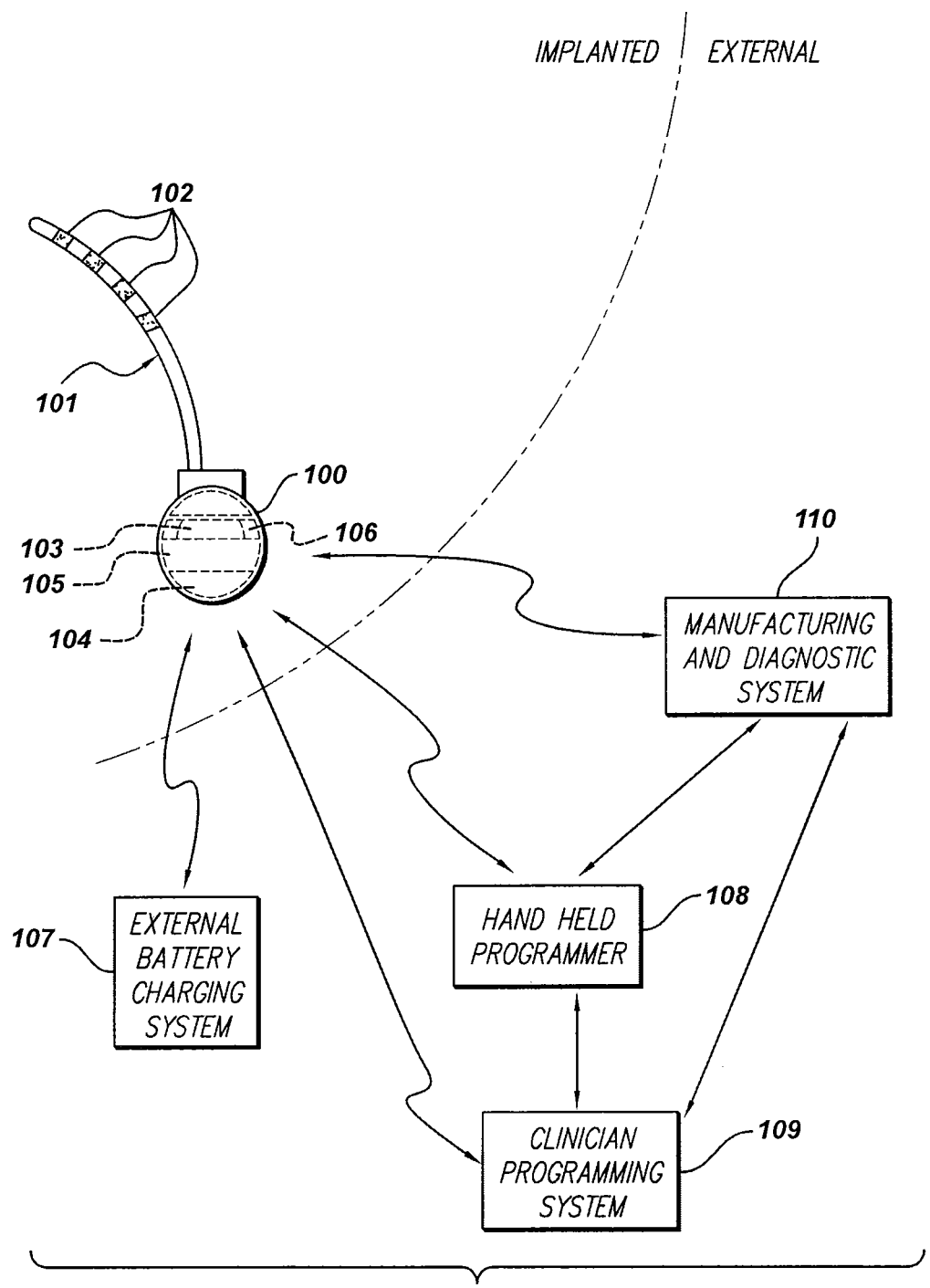
FIG. 1 illustrates an exemplary stimulator that may be used to apply electrical stimulation to one or more stimulation sites within a patient according to principles described herein.

To facilitate an understanding of the systems and methods described herein, a more detailed description of an implantable stimulator and its operation will now be given. FIG. 1 illustrates an exemplary stimulator 100 that may be used to apply electrical stimulation to one or more stimulation sites within a patient. The stimulation site may include any nerve or other tissue within the patient such as, but not limited to, a nerve within the spinal cord region.

In some examples, the exemplary stimulator 100 shown in FIG. 1 may include at least one lead 101 coupled thereto. In some examples, the at least one lead 101 includes a number of electrodes 102 through which electrical stimulation current may be applied to the stimulation site. It will be recognized that the at least one lead 101 may include any number of electrodes 102 arranged in any configuration as best serves a particular application. It will be recognized that the stimulator 100 may additionally or alternatively be coupled to one or more catheters through which one or more therapeutic drugs may be applied to the stimulation site.

As illustrated in FIG. 1, the stimulator 100 includes a number of components. It will be recognized that the stimulator 100 may include additional and/or alternative components as best serves a particular application. A power source 104 is configured to output voltage used to supply the various components within the stimulator 100 with power and/or to generate the power used for electrical stimulation. The power source 104 may include a primary battery, a rechargeable battery (e.g., a lithium-ion battery), a super capacitor, a nuclear battery, a mechanical resonator, an infrared collector (receiving, e.g., infrared energy through the skin), a thermally-powered energy source (where, e.g., memory-shaped alloys exposed to a minimal temperature difference generate power), a flexural powered energy source (where a flexible section subject to flexural forces is part of the stimulator), a bioenergy power source (where a chemical reaction provides an energy source), a fuel cell, a bioelectrical cell (where two or more electrodes use tissue-generated potentials and currents to capture energy and convert it to useable power), or the like.

The stimulator 100 may also include a coil 106 configured to receive and/or emit a magnetic field (also referred to as a radio frequency (RF) field) that is used to communicate with, or receive power from, one or more external devices. Such communication and/or power transfer may include, but is not limited to, transcutaneously receiving data from the external device, transmitting data to the external device, and/or receiving power used to recharge the power source 104.

For example, an external battery charging system (EBCS) 107 may be provided to generate power that is used to recharge the power source 104 via any suitable communication link. Additional external devices including, but not limited to, a hand held programmer (HHP) 108, a clinician programming system (CPS) 109, and/or a manufacturing and diagnostic system (MDS) 110 may also be provided and configured to activate, deactivate, program, and/or test the stimulator 100 via one or more communication links. It will be recognized that the communication links shown in FIG. 1 may each include any type of link used to transmit data or energy, such as, but not limited to, an RF link, an infrared (IR) link, an optical link, a thermal link, or any other energy-coupling link.

Additionally, if multiple external devices are used in the treatment of a patient, there may be communication among those external devices, as well as with the implanted stimulator 100. It will be recognized that any suitable communication link may be used among the various devices illustrated.

The external devices shown in FIG. 1 are merely illustrative of the many different external devices that may be used in connection with the stimulator 100. Furthermore, it will be recognized that the functions performed by any two or more of the external devices shown in FIG. 1 may be performed by a single external device.

The stimulator 100 may also include electrical circuitry 103 configured to generate the electrical stimulation current that is delivered to the damaged neural tissue via one or more of the electrodes 102. For example, the electrical circuitry 103 may include one or more processors, capacitors, integrated circuits, resistors, coils, and/or any other component configured to generate electrical stimulation current.

The stimulator 100 may also include a programmable memory unit 105 configured to store one or more stimulation parameters. The programmable memory unit 105 allows a patient, clinician, or other user of the stimulator 100 to adjust the stimulation parameters such that the stimulation applied by the stimulator 100 is safe and effective in treating a particular patient. The programmable memory unit 105 may include any type of memory unit such as, but not limited to, random access memory (RAM), static RAM (SRAM), a hard drive, or the like.

The stimulator 100 of FIG. 1 is illustrative of many types of stimulators that may be used in accordance with the systems and methods described herein. For example, the stimulator 100 may include an implantable pulse generator (IPG), a microstimulator, an external trial stimulator, or any other type of device configured to deliver electrical stimulation to a stimulation site within a patient. Exemplary IPGs suitable for use as described herein include, but are not limited to, those disclosed in U.S. Pat. Nos. 6,381,496, 6,553,263; and 6,760,626. Exemplary microstimulators suitable for use as described herein include, but are not limited to, those disclosed in U.S. Pat. Nos. 5,143,540; 5,312,439; 6,185,452; 6,164,284; 6,208,894; and 6,051,017. All of these listed patents are incorporated herein by reference in their respective entireties.

The lead 101 shown in FIG. 1 often has to be precisely implanted at an implant site located deep within the patient. To this end, a steerable stylet having a precurved distal portion may be used to help guide the lead 101 to the implant site. Described herein are various steerable stylet handle assemblies that may be used to facilitate handling of a steerable stylet.

Figure 2:
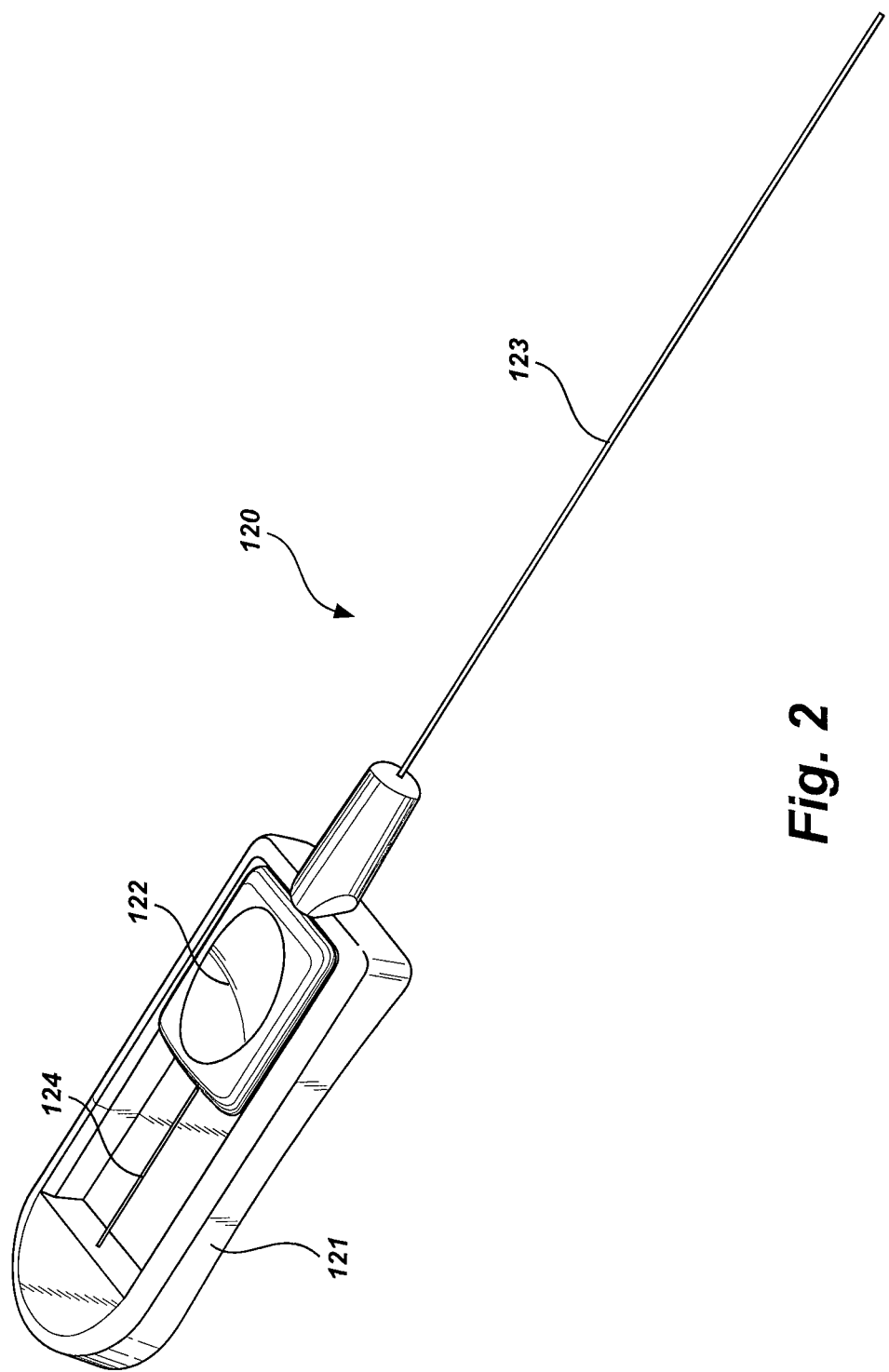
FIG. 2 is a perspective view of an exemplary steerable stylet handle assembly according to principles described herein.

FIG. 2 is a perspective view of an exemplary steerable stylet handle assembly 120. As shown in FIG. 2, the handle assembly 120 includes a handle housing 121, a movable button 122, and a stylet subassembly comprising an outer tubing 123 and an inner stylet wire 124 having a distal portion that assumes a pre-curved shape when not covered by the outer tubing 123. Each of these components will be described in more detail below.

Figure 3:
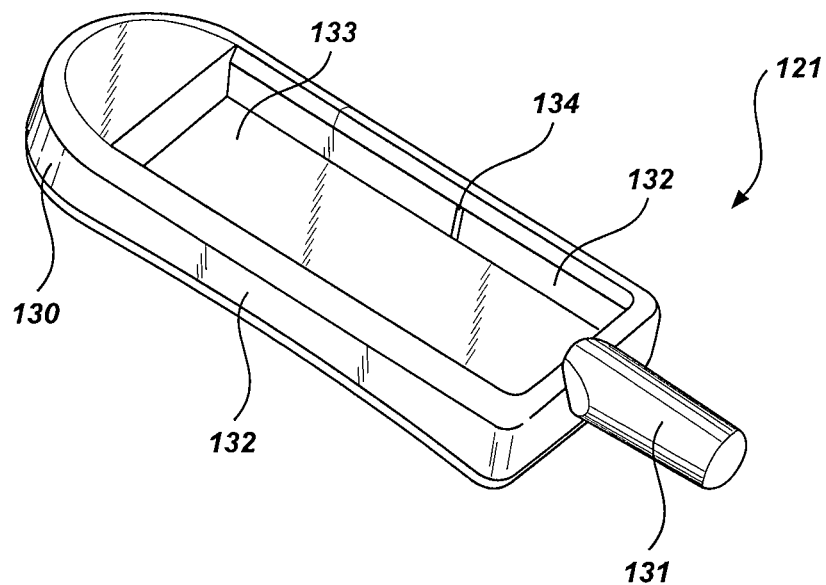
FIG. 3 is a perspective side view of the handle housing according to principles described herein.

FIG. 3 is a perspective side view of the handle housing 121. As shown in FIG. 3, the housing 121 includes a main body 130 and a throat portion 131 having a lumen extending therethrough.

The main body 130 of the handle housing 121 includes side walls 132 that define a channel 133 configured to receive the button 122, as will be described in more detail below. The main body 130 may also include one or more mating ribs 134 molded into one or both of the inner side walls 132 of the housing. The mating ribs 134, as will be described in more detail below, are configured to mate with corresponding one or more ratchets molded into the button 122.

The throat portion 131, as shown in FIG. 3, is disposed at the distal end of the main body 130. The lumen extending through the throat portion is in communication with the housing channel 133 and, as will be described in more detail below, is configured to allow passage therethrough of the stylet subassembly.

The handle housing 121 may be made out of any suitable material as may serve a particular application. For example, the entire housing 121 may be plastic molded. In this manner, a simple injection mold process may be used to construct the entire housing 121.

It will also be recognized that the handle housing 121 may have any suitable shape that facilitates holding thereof with one hand. For example, handle housing 121 may be shaped to allow the physician's or other handler's index and middle fingers to support the underside of the main body 130 while the handler's thumb is positioned on top of the button 122.

In some examples, the main body 130 of the handle housing 121 may be generally rectangular, as shown in FIG. 3. However, it will be recognized that the main body 130 may have any other suitable shape as may serve a particular application. In some examples, the bottom surface and/or one or more of the side walls 132 of the main body 130 may be slightly contoured so as to allow the hand more naturally grip the housing 121.

Figure 4:
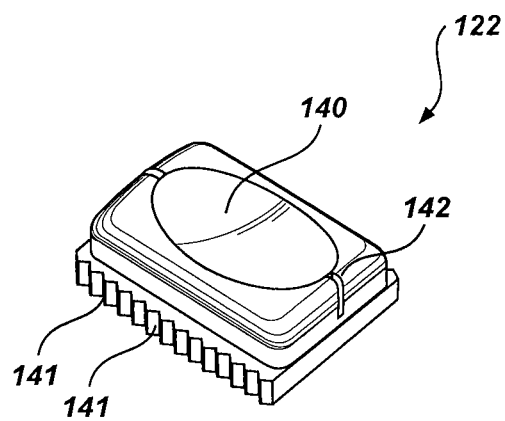
FIG. 4 is a perspective view of the handle assembly button according to principles described herein.

FIG. 4 is a perspective view of the handle assembly button 122. As shown in FIG. 4, the button 122 may include a shallow depression 140 configured to facilitate placement thereon of the handler's thumb. However, it will be recognized that the button 122 does not necessarily have to include the shallow depression 140 and that it may alternatively include any other type of surface as may serve a particular application.

As shown in FIG. 4, the button 122 may include a series of ratchets 141 molded into one or more sidewalls thereof. As will be described in more detail below, the ratchets 141 are configured to engage with the one or more mating ribs 134 that are a part of the housing 121.

The button 122 may also include a lumen 142 extending therethrough. As will be described in more detail below, the outer tubing 123 and/or inner stylet wire 124 of the stylet subassembly are configured to at least partially pass through the lumen 132 of the button 122.

In some examples, the button 122 is dimensioned to snap fit into the channel 133 of the housing 121 and may be made out of any suitable material as may serve a particular application. For example, the button 122 may be plastic molded using a simple injection mold process.

Figure 5:
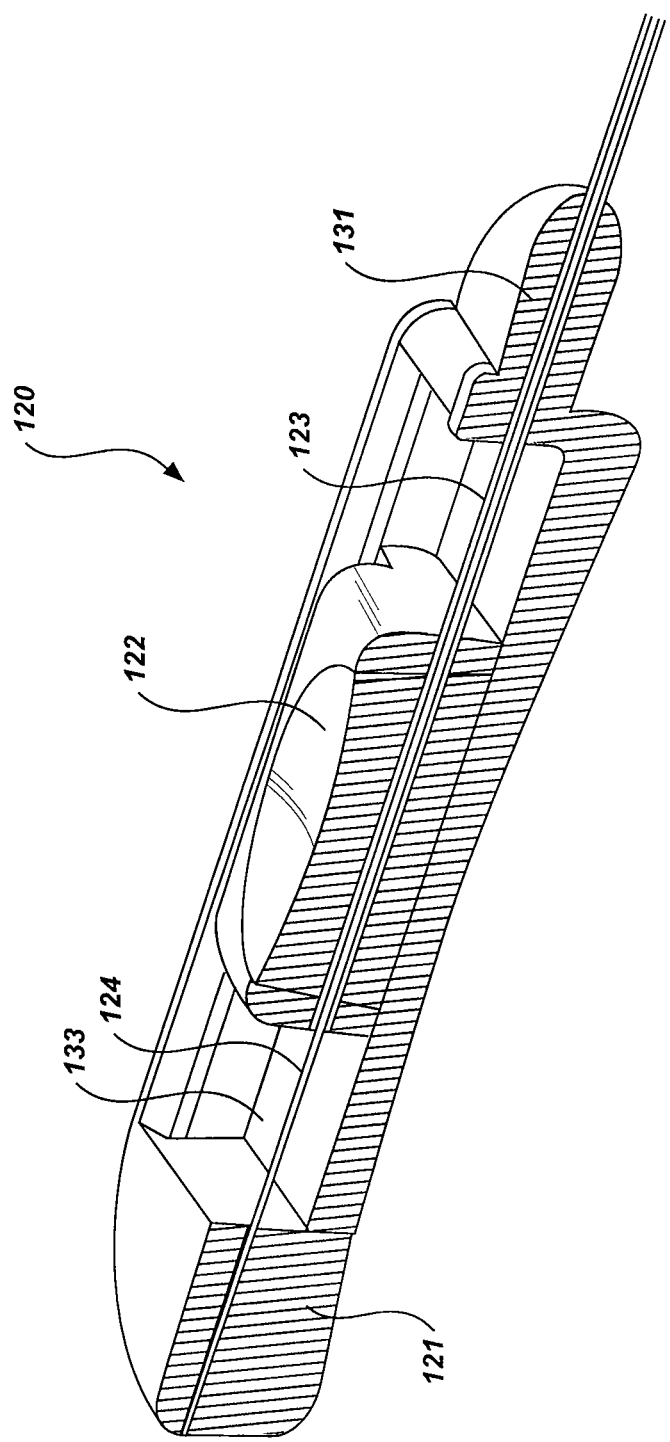
FIG. 5 is a cross sectional side view of the steerable stylet handle assembly according to principles described herein.

FIG. 5 is a cross sectional side view of the steerable stylet handle assembly 120 and shows how the outer tubing 123 and the inner stylet wire 124 of the stylet subassembly are coupled to the handle assembly 120.

As shown in FIG. 5, the inner stylet wire 124 passes through the lumen of the throat portion 131, into the channel 133 of the housing 121, and through the lumen of the button 122. The proximal portion of the inner stylet wire 124 is securely coupled to an inside rear portion of the handle housing 121. The wire 124 may be securely coupled to the housing 121 via an adhesive bond, mechanical attachment (e.g., an interference fit or crimp), or any other suitable attachment means.

The outer tubing 123, as shown in FIG. 5, also passes through the lumen of the throat portion 131 and into the channel 133 of the housing 121. The outer tubing 123 may then at least partially pass through the lumen of the button 122 before it is securely coupled to the button 122. In some alternative examples, the outer tubing 123 is securely coupled to the button 122 without passing through the button's lumen. The outer tubing 123 may be securely coupled to the button 122 via an adhesive bond, mechanical attachment (e.g., an interference fit or crimp), or any other suitable attachment means.

The button 122 is configured to be able to move forwards (distally) and backwards (proximally) within the channel 133 of the housing 121 in response to pressure applied by the thumb of the handler. Because the outer tubing 123 is securely coupled to the button 122, the outer tubing 123 moves distally and proximally in conjunction with the movement of the button 122. The movement of the outer tubing 123 relative to the stationary inner stylet wire 124 may alternatively expose or cover the pre-curved distal portion of the stylet wire 124, as will be described in more detail below.

Figure 6:
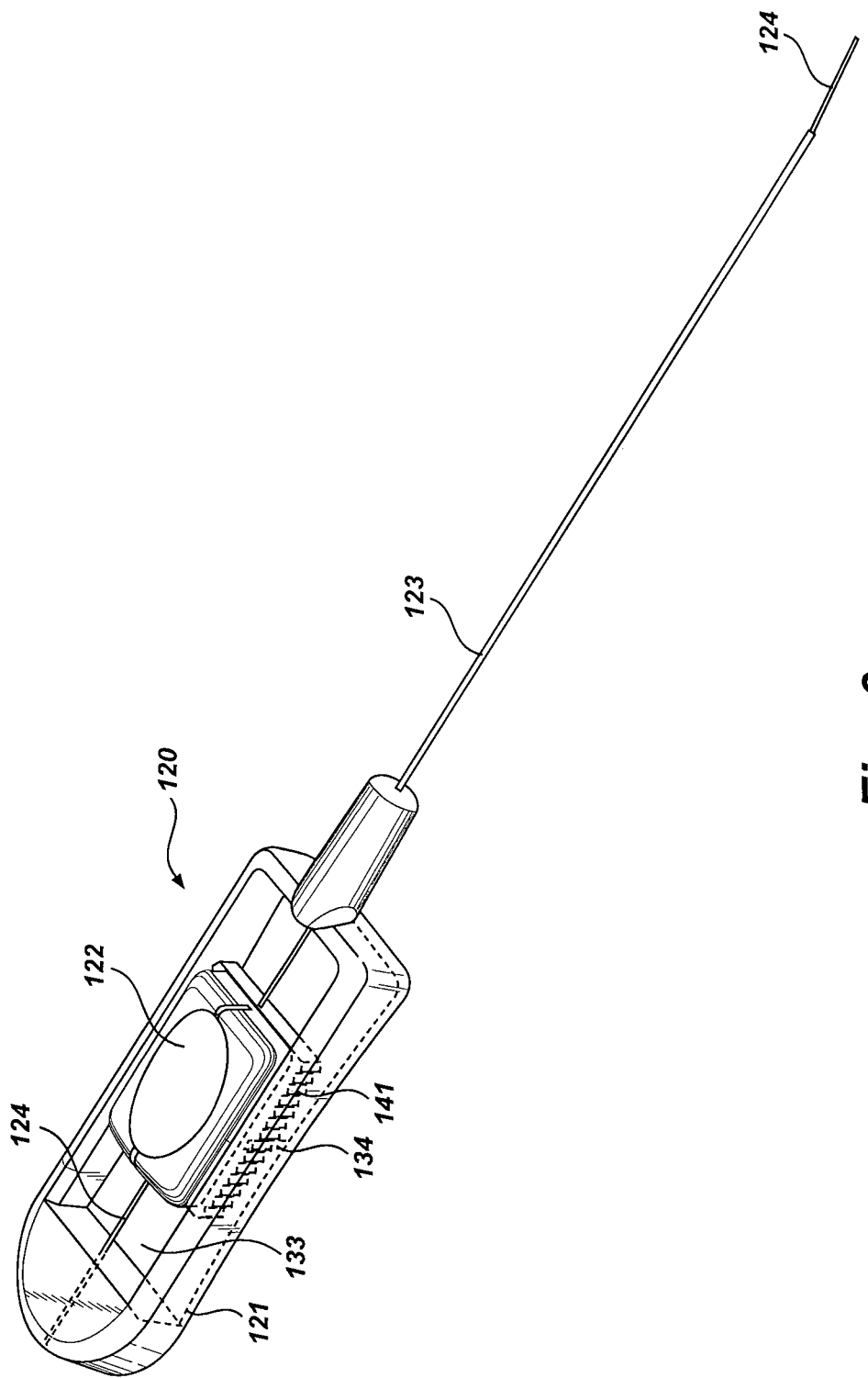
FIG. 6 is a perspective wireframe view of the steerable stylet handle assembly according to principles described herein.

FIG. 6 is a perspective wireframe view of the steerable stylet handle assembly 120 and shows the effect of moving the button 122 within the channel 133 of the housing 121. As shown in FIG. 6, the mating rib 134 located on one of the side walls 132 of the housing 121 is configured to engage one of the ratchets 141 that are a part of the button 122. In this manner, the position of the button 122, and consequently the outer tubing 123, may be stabilized at one position. By applying pressure with the thumb to the button 122, the engagement between the mating rib 134 and the ratchet 141 may be overridden and the button 122 may be moved distally or proximally as desired. It will be recognized that the button 122 may alternatively include one or more mating ribs 134 and that one or more of the side walls 132 may alternatively include the series of ratchets 141.

To illustrate, FIG. 6 shows the button 122 after it has been moved proximally (i.e., retracted) to expose the pre-curved distal portion of the inner stylet wire 124. In some examples, when the button 122 is moved proximally, the outer tubing 123 also moves proximally, thereby exposing the pre-curved distal portion of the inner stylet wire 124. Likewise, when the button 122 is moved distally, the outer tubing 123 also moves distally and covers the pre-curved distal portion of the inner stylet wire 124.

In this manner, a physician may control the amount of deflection or curvature that the pre-curved distal portion of the inner stylet wire 124 assumes by adjusting the position of the outer tubing 123 with the button 122. To straighten or lessen the amount of curvature of the pre-curved distal portion of the inner stylet wire 124, the button 122 is advanced forward or distally. To increase the amount of curvature of the pre-curved distal portion of the inner stylet wire 124, the button 122 retracted backwards or proximally.

The physician may also turn the wire 124 about the axis of the outer tube 123 by rotating the housing 121 about the same axis. In this manner, the stylet wire 124 may be used to more accurately position a lead at a desired location within the body.

The inner stylet wire 124 may be made out of any suitable material with shape memory (e.g., stainless steel). The outer tube 123 may also be made out of any suitable material as may serve a particular application.

Figure 7:
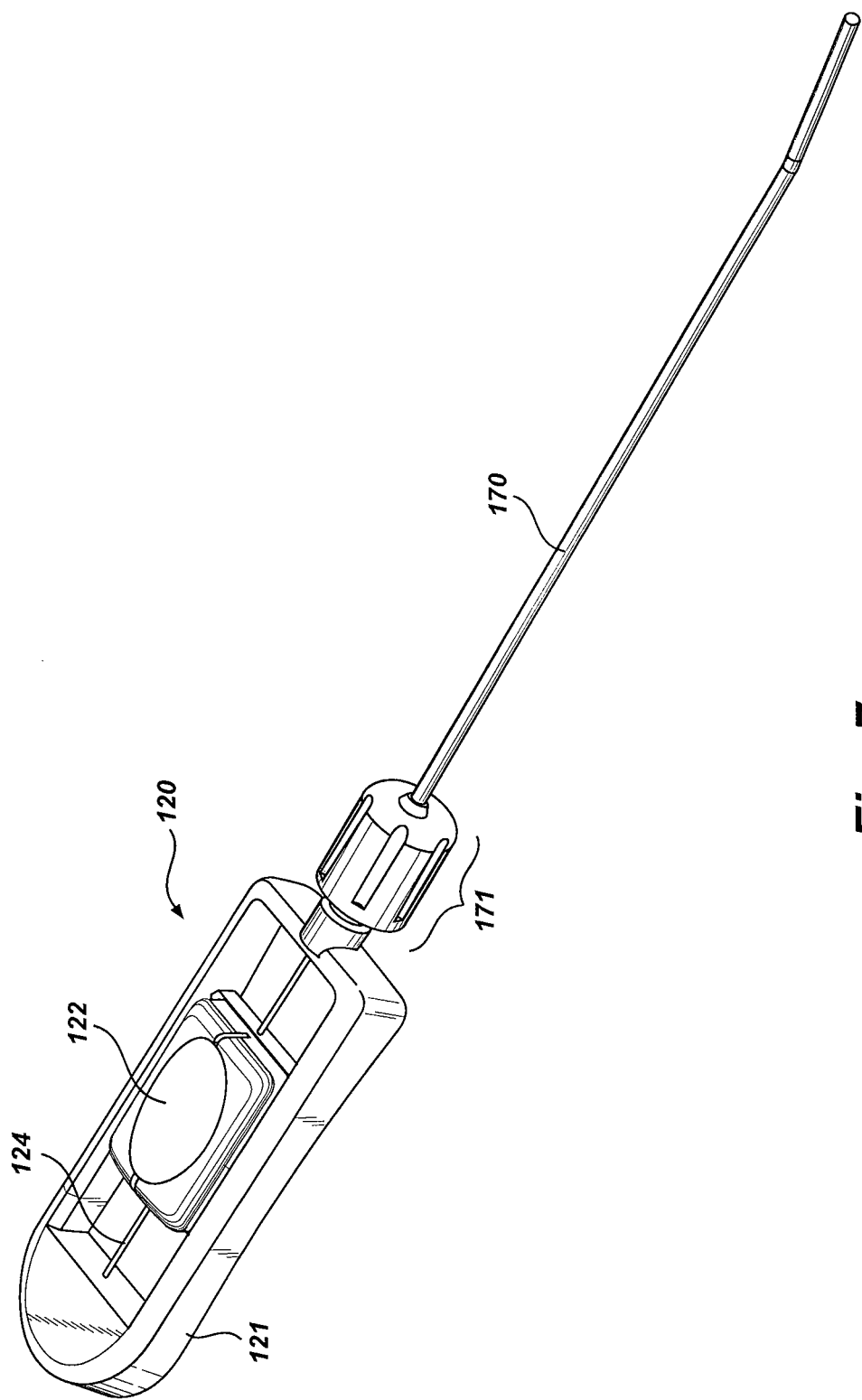
FIG. 7 illustrates a configuration wherein a stimulating member is placed over the stylet subassembly of the steerable stylet handle assembly according to principles described herein.

FIG. 7 illustrates a configuration wherein a stimulating member 170 is placed over the stylet subassembly of the steerable stylet handle assembly 120. The stimulating member 170 may include a lead with electrodes disposed thereon, a catheter, or any other stimulating member as may serve a particular application. As shown in FIG. 7, the handle assembly 120 may include a locking mechanism 171 configured to lock the proximal portion of the stimulating member 170 to the housing 121 of the handle assembly 120.

Figure 8A:
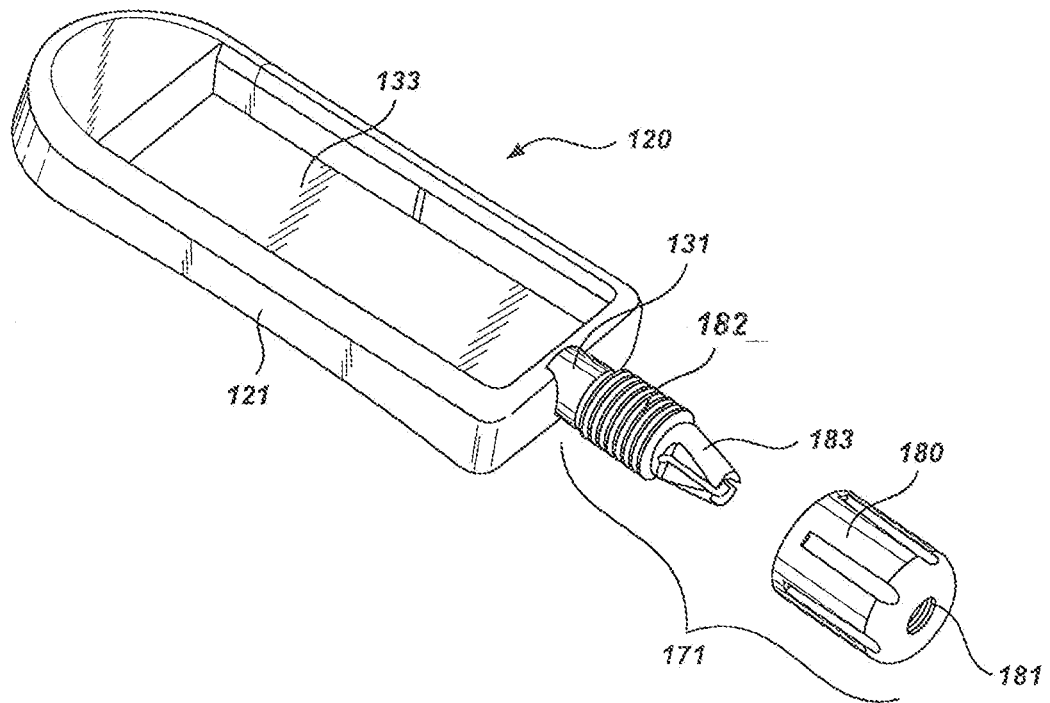
FIG. 8A is an exploded perspective view of a locking mechanism according to principles described herein.
Figure 8B:
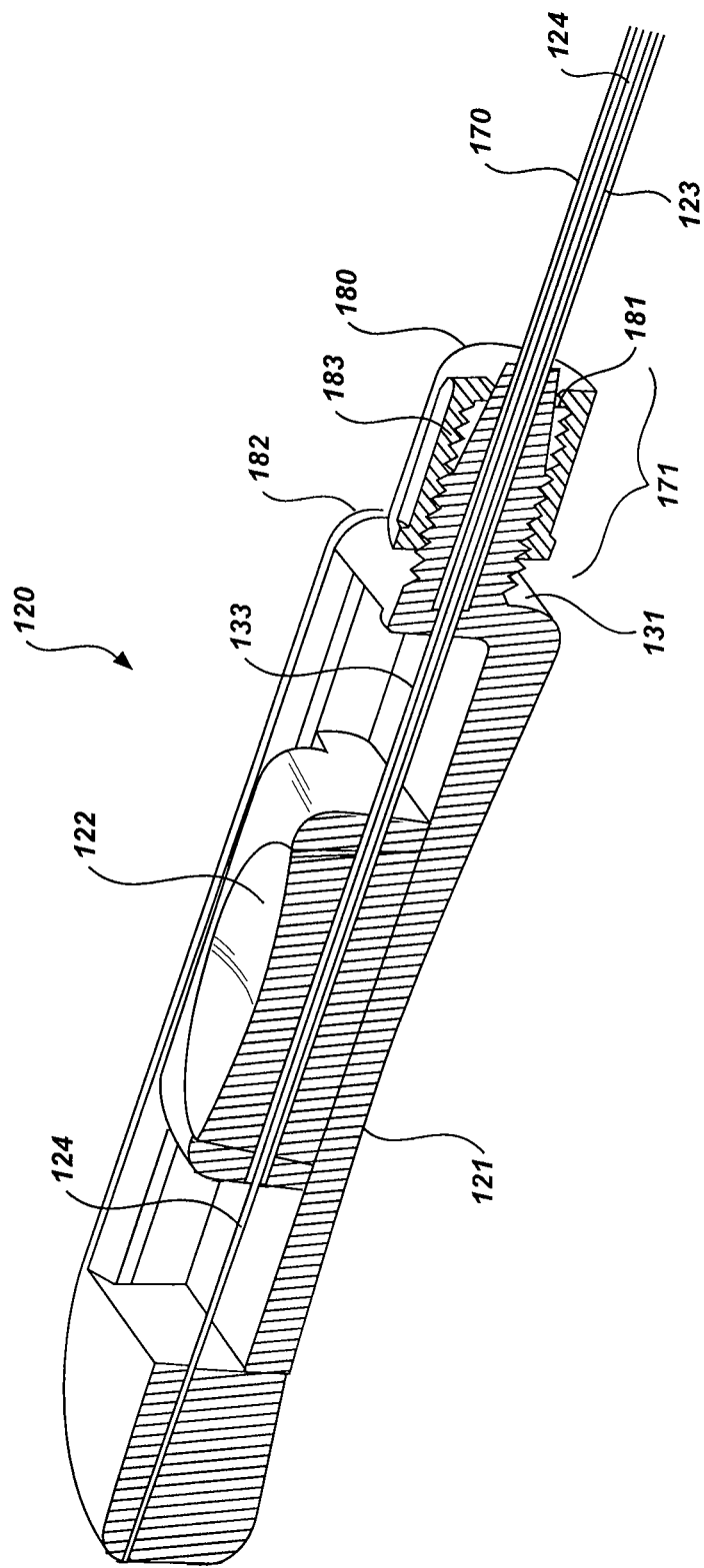
FIG. 8B is a cross sectional side view of the locking mechanism shown in FIG. 8A according to principles described herein.

FIG. 8A is an exploded perspective view of the locking mechanism 171 and FIG. 8B is a cross sectional side view of the locking mechanism 171. As shown in FIGS. 8A-8B, the locking mechanism 171 may include a nut 180 with mating internal screw threads 181 configured to mate with external screw threads 182 molded into the throat portion 131 of the housing 121. The throat portion 171 may also include a split tapered chuck 183 molded integrally with the throat portion 131. The stimulating member 170 is secured to the housing 121 by inserting the proximal portion of the stimulating member 170 into the opening of the split tapered chuck 183 and then tightening the nut 180. The tightening of the nut 180 causes the split tapered chuck 183 to compress and grip the stimulating member 170. In this manner, the stimulating member 170 may be prevented from advancing forward relative to the stationery inner stylet wire 124 when the button 122 is advanced forward to straighten the pre-curved distal portion of the inner stylet wire 124.

The preceding description has been presented only to illustrate and describe embodiments of the invention. It is not intended to be exhaustive or to limit the invention to any precise form disclosed. Many modifications and variations are possible in light of the above teaching.

What is claimed is:

1. A steerable stylet handle assembly, comprising:
   a housing having first and second side walls defining a channel therebetween;
   a button in communication with said first and second side walls and configured to move distally and proximally within said channel;
   a stylet subassembly comprising an outer tubing and an inner stylet wire located at least partially within the outer tubing, said inner stylet wire having a pre-curved distal portion;
   wherein a proximal portion of said inner stylet wire is coupled to a proximal portion of said housing and a proximal portion of said outer tubing is coupled to said button and configured and arranged so that movement of the button distally and proximally within the channel results in a corresponding movement of the outer tubing; and
   wherein movement of said button within said channel is configured to move the outer tubing to selectively expose and cover at least a portion of said pre-curved distal portion of said inner stylet wire with said outer tubing.

2. The handle assembly of claim 1, wherein said button comprises a lumen through which said inner stylet wire and outer tubing at least partially pass.

3. The handle assembly of claim 1, wherein at least a portion of said pre-curved distal portion of said inner stylet wire is exposed when said button is moved proximally within said channel.

4. The handle assembly of claim 1, wherein at least a portion of said pre-curved distal portion of said inner stylet wire is covered when said button is moved distally within said channel.

5. The handle assembly of claim 1, wherein said button comprises one or more ratchets configured to mate with one or more mating ribs that are a part of one or more of said side walls of said housing.

6. The handle assembly of claim 1, wherein said button is configured to move within said channel in response to pressure applied by a thumb of a handler of said handle assembly.

7. The handle assembly of claim 1, wherein said housing comprises a throat portion disposed at a proximal end thereof, said throat portion comprising a lumen passing therethrough in communication with said channel.

8. The handle assembly of claim 7, further comprising a locking mechanism configured to secure a stimulating member to said throat portion.

9. The handle assembly of claim 8, wherein said locking mechanism comprises a split tapered chuck and a nut.

10. The handle assembly of claim 8, wherein said stimulating member comprises a lead or a catheter.

11. A system for facilitating stimulation of a stimulation site within a patient, said system comprising:
    a lead having at least one electrode disposed thereon; and
    a steerable stylet handle assembly configured to implant said at least one electrode at said stimulation site comprising
    a housing having first and second side walls defining a channel therebetween;
    a button in communication with said first and second side walls and configured to move distally and proximally within said channel;
    a stylet subassembly configured to be inserted within said lead and comprising an outer tubing and an inner stylet wire located at least partially within the outer tubing, said inner stylet wire having a pre-curved distal portion;
    wherein a proximal portion of said inner stylet wire is coupled to a proximal portion of said housing and a proximal portion of said outer tubing is coupled to said button and configured and arranged so that movement of the button distally and proximally within the channel results in a corresponding movement of the outer tubing; and
    wherein movement of said button within said channel is configured to position said at least one electrode at said stimulation site by moving the outer tubing to selectively expose and cover at least a portion of said pre-curved distal portion of said inner stylet wire with said outer tubing.

12. The system of claim 11, wherein said button comprises a lumen through which said inner stylet wire and outer tubing at least partially pass.

13. The system of claim 11, wherein at least a portion of said pre-curved distal portion of said inner stylet wire is exposed when said button is moved proximally within said channel.

14. The system of claim 11, wherein at least a portion of said pre-curved distal portion of said inner stylet wire is covered when said button is moved distally within said channel.

15. The system of claim 11, wherein said button comprises one or more ratchets configured to mate with one or more mating ribs that are a part of one or more of said side walls of said housing.

16. The system of claim 11, wherein said button is configured to move within said channel in response to pressure applied by a thumb of a handler of said handle assembly.

17. The system of claim 11, wherein said housing comprises a throat portion disposed at a proximal end thereof, said throat portion comprising a lumen passing therethrough in communication with said channel.

18. The system of claim 17, further comprising a locking mechanism configured to secure said lead to said throat portion.

19. The system of claim 18, wherein said locking mechanism comprises a split tapered chuck and a nut.

20. A method, comprising:
- providing a housing having first and second side walls defining a channel therebetween;
- providing a button in communication with said first and second side walls and configured to move distally and proximally within said channel;
- providing a stylet subassembly comprising an outer tubing and an inner stylet wire located at least partially within the outer tubing, said inner stylet wire having a pre-curved distal portion;
- coupling a proximal portion of said inner stylet wire to a proximal portion of said housing;
- coupling a proximal portion of said outer tubing to said button so that movement of the button distally and proximally within the channel results in a corresponding movement of the outer tubing; and
- moving said button within said channel to move the outer tubing to selectively expose and cover at least a portion of said pre-curved distal portion of said inner stylet wire with said outer tubing.

* * * * *